(12) United States Patent
Malmin (10) Patent No.: US 8,340,386 B2
(45) Date of Patent: Dec. 25, 2012

(54) SYSTEM AND METHOD FOR MEASURING HOLE ORIENTATION FOR SPECT COLLIMATORS

(75) Inventor: Ronald E. Malmin, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 154 days.

(21) Appl. No.: 12/987,376

(22) Filed: Jan. 10, 2011

(65) Prior Publication Data

US 2012/0177268 A1    Jul. 12, 2012

(51) Int. Cl.
*G06K 9/00* (2006.01)
*A61B 6/00* (2006.01)

(52) U.S. Cl. ........................... 382/131; 382/274; 378/19

(58) Field of Classification Search .................. 382/100, 382/103, 106, 128, 129, 130, 131, 132, 133, 382/134, 162, 168, 173, 181, 232, 254, 274, 382/276, 305, 312; 250/363.04; 378/4, 19, 378/21
See application file for complete search history.

(56) References Cited

U.S. PATENT DOCUMENTS

| | | | |
|---|---|---|---|
| 4,958,081 A | 9/1990 | Malmin et al. | |
| 5,565,684 A * | 10/1996 | Gullberg et al. | 250/363.04 |
| 6,771,732 B2 * | 8/2004 | Xiao et al. | 378/4 |
| 7,385,200 B2 * | 6/2008 | Vija | 250/363.04 |
| 8,116,427 B2 * | 2/2012 | Kojima et al. | 378/19 |
| 2010/0054571 A1 * | 3/2010 | Kojima et al. | 382/131 |

* cited by examiner

*Primary Examiner* — Seyed Azarian
(74) *Attorney, Agent, or Firm* — Peter Kendall (57) ABSTRACT

A method for measuring a SPECT collimator's hole orientation angles includes (a) providing a plurality of parallel spaced apart line radiation sources at a distance from a detector; (b) positioning a first collimator between the plurality of spaced apart line radiation sources and the detector; (c) obtaining a set of line images of the plurality of line radiation sources by scanning/stepping the plurality of line radiation sources across the first collimator in a first direction; (d) obtaining a second set of line images of the plurality of line radiation sources by scanning/stepping the plurality of line radiation sources across the first collimator in a second direction thai is perpendicular to the first direction; (e) repeating the steps (c) and (d) for a second collimator, wherein one of the two collimators is a reference collimator and the other of the two collimators is a collimator being measured.

14 Claims, 5 Drawing Sheets

SYSTEM AND METHOD FOR MEASURING HOLE ORIENTATION FOR SPECT COLLIMATORS

FIELD OF THE DISCLOSURE

The disclosure generally relates to the field of image reconstruction, and more particularly, to a system and method for compensating for inaccuracies in collimator hole geometries to provide reduced distortion and improved resolution of tomographic images.

BACKGROUND

Single Photon Emission Computed Tomography (SPECT) reconstructs three dimensional images of radioactive source distributions in the body using a sequence of planar images acquired over a range of angles around the patient.

In order to reconstruct the tomographic image from the set of planar images it is necessary to know the direction from which the photons detected at a given point in the image originated. For X-ray computed tomography (CT), the direction is defined by a line from the anode to the X-ray detector. For Positron Emission Tomography (PET), it is a line between the pair of detectors in which the two coincident 511 keV photons are detected. In SPECT, the direction is usually defined by a collimator—a lead plate with 20,000 to 50,000 small holes formed in it which restricts the detected incident photons to only those with known angles of incidence at the detector.

The most popular collimator type is the parallel beam collimator, in which the holes are designed to point perpendicular to the detector surface. Another type of collimator is referred to as a fan beam collimator. With the fan beam collimator, the holes in one dimension (transverse) focus to a point; there is no focusing in the axial dimension. A further type of collimator is referred to as a cone beam collimator. The cone beam collimator focuses to a single point in both transverse and axial dimensions.

Reconstruction algorithms in the current state of the art assume that the construction of these collimators is perfect. Such algorithms perform back projection of planar projection data and forward projections of the object estimates under this assumption. In reality, however, collimators are not perfect. Their construction is subject to dimensional errors such that all holes do not point in the ideal intended direction. This leads to errors in forward and backward projections and, results in distortions and degradation of the resolution in the final tomographic images.

Therefore, there is a need for an improved method for accounting for inaccuracies in the collimator hole pointing directions, and for employing this accounting in the reconstruction process to remove distortions and improve the resolution of reconstructed images.

SUMMARY

The disclosed system and method improve the quality of reconstructed images by performing forward and/or back projections using a vector map of the hole directions at each point of the collimator surface. This approach will work for arbitrary collimation geometry and will automatically account for errors in the collimator "pointing vectors," thereby minimizing distortions and improving reconstructed image resolution.

An exemplary technique is disclosed for mapping the hole directions over the entire surface of the collimator. The technique is applicable to arbitrary collimator geometries. A specific example is given for the multi focal collimator—a variable focal length fan in two independent dimensions—however, it will be appreciated that the system and method can be used with any collimator type.

According to an implementation of the present disclosure, a method for measuring a SPECT collimator's hole orientation angles is disclosed. The method comprises: (a) providing a plurality of parallel spaced apart line radiation sources at a distance from a detector; (b) positioning a first collimator between the plurality of spaced apart line radiation sources and the detector; (c) obtaining a set of line images of the plurality of line radiation sources by scanning/stepping the plurality of line radiation sources across the first collimator in a first direction; (d) obtaining a second set of line images of the plurality of line radiation sources by scanning/stepping the plurality of line radiation sources across the first collimator in a second direction that is perpendicular to the first direction; (e) repeating the steps (c) and (d) for a second collimator, wherein one of the two collimators is a reference collimator and the other of the two collimators is a collimator being measured, whereby the line images obtained using the reference collimator are reference collimator line images and the line images obtained using the collimator being measured are measured collimator line images; (f) analyzing the reference collimator line images and the measured collimator line images and determining the offset distance dx between the reference collimator line images and the measured collimator line images in the first direction and the offset distance dy between the reference collimator line images and the measured collimator line images in the second direction, wherein dx is the offset distance in the first direction and dy is the offset distance in the second direction; and (g) calculating hole orientation angles $\theta x$, $\theta y$ for each collimator hole in the collimator being measured.

According to another implementation, a method for measuring a SPECT collimator's hole orientations comprises: (a) providing a plurality of parallel spaced apart line radiation sources at a distance from a detector; (b) positioning a collimator to be measured between the plurality of spaced apart line radiation sources and the detector; (c) obtaining a first set of line images of the plurality of line radiation sources by scanning/stepping the plurality of line radiation sources at a plurality of stepped positions across the collimator in a first direction; (d) obtaining a second set of line images of the plurality of line radiation sources by scanning/stepping the plurality of line radiation sources at a plurality of stepped positions across the collimator in a second direction that is orthogonal to the first direction, whereby the line images obtained using the collimator being measured are measured collimator line images; (e) determining a reference position for each of the measured collimator line image from the stepped positions of the plurality of line radiation sources measured with respect to the detector; (f) analyzing the measured collimator line images and determining the offset distances dx between the reference position and the measured collimator line images for each measured collimator line images in the first direction and the offset distances dy between the reference position and the measured collimator line images for each measured collimator line images in the second direction; and (g) calculating hole orientation angles $\theta x$, $\theta y$ for each collimator hole in the collimator being measured.

According to another aspect, the present disclosure provides a method for reconstruction of single photon emission computed tomographic images wherein forward and/or backward projection procedures in the reconstruction utilizes actual measured SPECT collimator hole orientation angles, whereby the reconstructed tomographic images have improved image resolution.

BRIEF DESCRIPTION OF THE DRAWINGS

The details of the invention, both as to its structure and operation, may be obtained by a review of the accompanying drawings, in which like reference numerals refer to like parts, and in which.

DETAILED DESCRIPTION

Figure 1A:
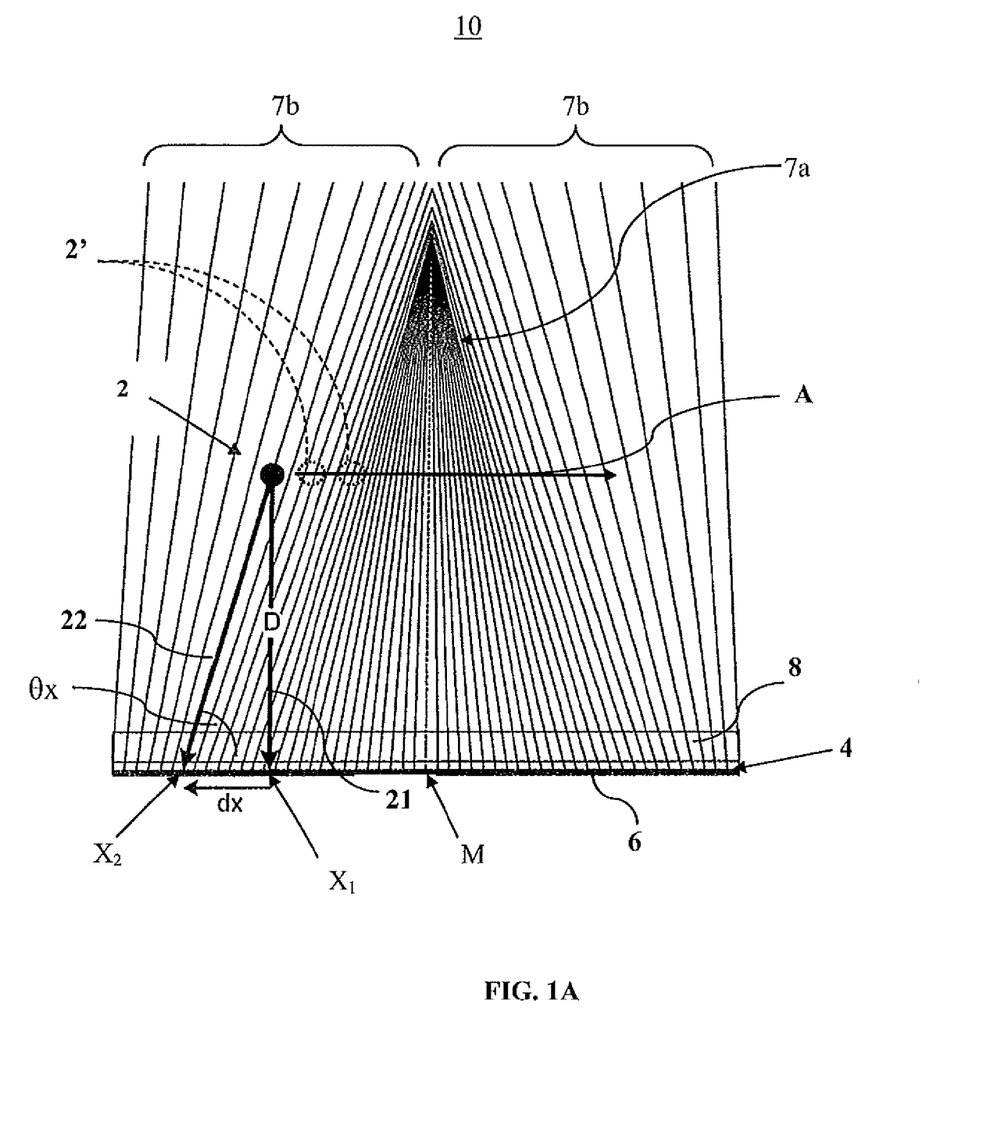
FIG. 1A shows a schematic representation of an arrangement for determining collimator hole angle using scanning radioactive line sources.

FIG. 1A shows a schematic of an arrangement 10 for use in measuring the hole angles of a collimator 8. The arrangement 10 allows measuring the collimator hole angles using one or more line radiation sources 2. The measured collimator hole angles are then compiled into a vector map providing the orientation of the holes in the collimator 8 that can be incorporated into the forward and/or backward projection steps of tomographic reconstruction in SPECT imaging. Knowing the actual orientation of the collimator holes rather than assuming that they are oriented in the intended ideal orientation makes the forward and backward projection process more accurate.

The method of measuring the orientation of the collimator holes will now be described in conjunction with the FIGS. 1A-6. Referring to FIG. 1A, a line radiation source 2 is positioned a known distance D above the interaction plane 4 of a medical imaging detector 6. A collimator 8, whose hole angles are to be measured, e.g. a multi-focal length collimator, is positioned between the line radiation source 2 and the detector 6. The line radiation source 2 is configured and adapted to be controllably movable or scanned in a direction A parallel to the interaction plane 4 of the detector 6 so that the line radiation source 2 maintains its distance D above the detector's interaction plane 4.

Figure 2:
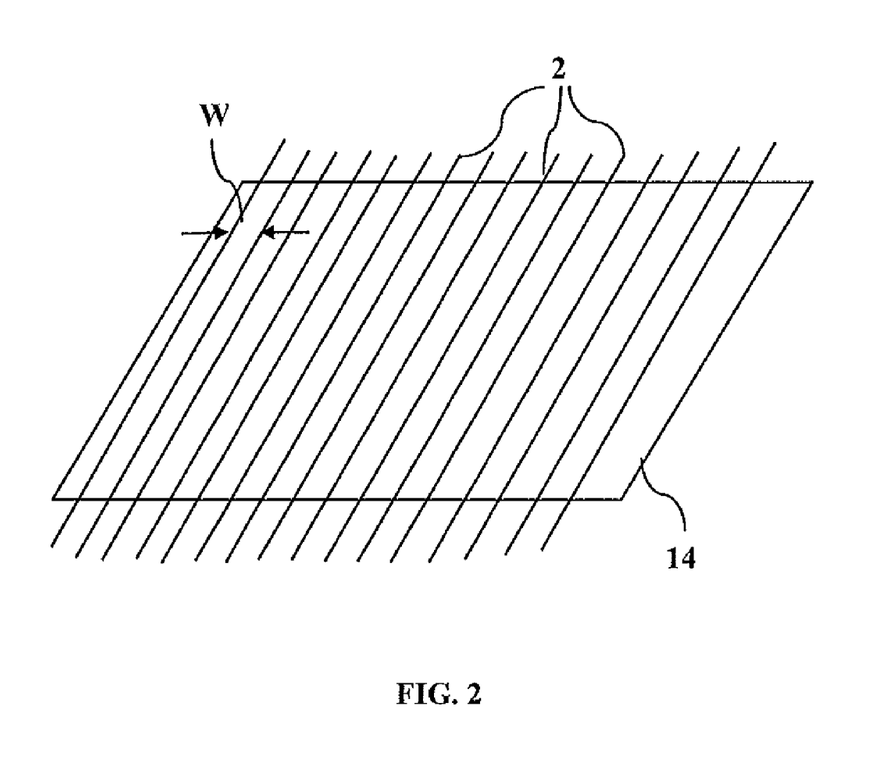
FIG. 2 is a schematic illustration of a carrier holding a set of a plurality of line radiation sources.

FIG. 1A shows only one line radiation source 2 viewed from one end of the line radiation source 2 for purpose of simplifying the description. In practical application, however, for matter of efficiency, a plurality of line radiation sources are used to minimize the time required to make the measurements. For example, FIG. 2 shows a carrier 14 on which is provided a plurality of the line radiation sources 2. The plurality of line radiation sources 2 are in parallel arrangement and they are a set distance W apart. The absolute value of the spacing distance W is arbitrary but it is a fixed value for a given set of line radiation sources 2. The line radiation sources 2 are filled with an appropriate isotope. In one embodiment, a total of twenty line radiation sources filled with technetium isotope are used. It will be appreciated that other isotopes, and a greater or lesser number of line sources may also be used.

Figure 1B:
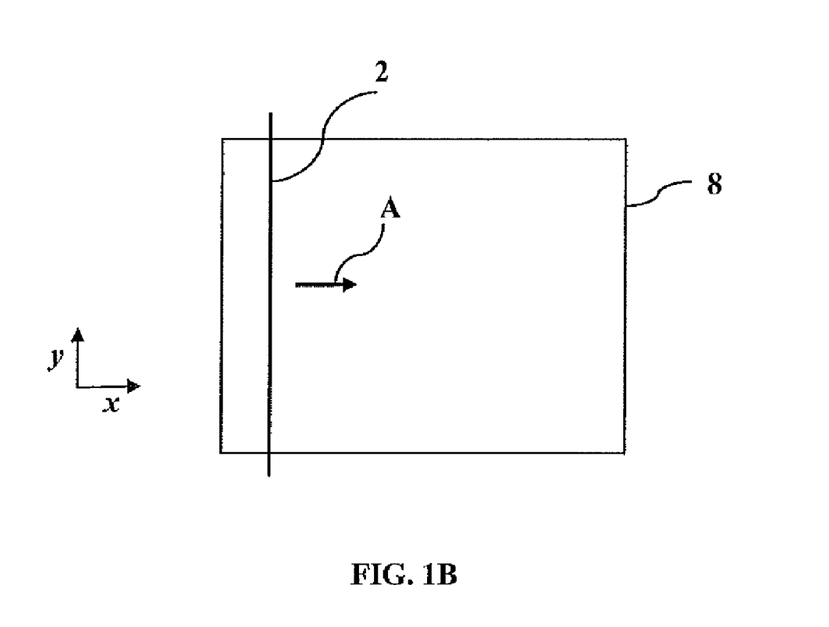
FIG. 1B shows a top-down schematic view of a collimator and a scanning radioactive line source illustrating the orientation and scanning direction of the line source with respect to the collimator.

FIG. 1B shows a schematic top-down view of the arrangement 10 showing a line radiation source 2 above the collimator 8. The collimator 8 is a 2-dimensional array of holes that extend in parallel rows in the x and y directions noted in the drawing. The holes' locations are defined in an x-y coordinate as shown and the line radiation source 2 is configured to be parallel to one of the x or y axes of the collimator 8 and movable in direction A that is perpendicular to the line radiation source. In the illustrated example, the line radiation source 2 is parallel to the y axis and is being scanned along the direction A which is orthogonal to the y axis and parallel to the x axis. Thus, the view shown in FIG. 1A shows the arrangement 10 along the x axis.

Using the illustration of FIG. 1A, measuring the orientation angle of one hole in the collimator 8 along the x axis will be described. In the illustrated example, the collimator 8 is a variable focal length fan beam collimator as represented by the hole orientation lines 7. The holes of the collimator 8 are configured to form an approximately fan beam region 7a and variable focal length regions 7b.

First, an image of the line radiation source 2 is taken using the detector 6 through the variable focal length fan beam collimator 8. The detector will see the line radiation source 2 through a set of detector pixels located near $X_2$ on the detector 6 which have a direct line of sight to the line radiation source 2 through the collimator 8. By this, we mean that a set of detector pixels detect the radiation beam 22 from the line radiation source 2 through a set of collimator holes that are aligned between the line radiation source 2 and the detector pixels near the position $X_2$. We refer to sets of detector pixels near the position $X_2$ rather than a single detector pixel because collimator holes at multiple positions $X_2$ can view, at least partially, the source 2, leading to a distribution of energized pixels with peaked energized pixels at $X_2$. Thus, the image of the line radiation source 2 is detected by the detector pixels near position $X_2$ that are displaced by a distance dx from a reference position $X_1$ that is directly under the line radiation source 2. The position $X_2$ will be referred to herein as the measured position.

Next, another image of the line radiation source 2 is taken using the detector 6 through a parallel hole reference collimator (not shown). Because the holes in the parallel hole reference collimator are oriented orthogonal to the plane of the collimator, the detector will see the line radiation source 2 through a set of detector pixels located near the reference position $X_1$ by detecting the radiation beams traveling along the line 21 and impinging on the detector pixels. Thus, by comparing the two line images, the offset distance dx between the reference position $X_1$ and the measured position $X_2$ can be measured.

Because the line radiation source 2 is always at a distance D from the detector's surface 4, as illustrated in FIG. 1A, we see that the arrangement of the line radiation source 2, $X_1$ and $X_2$ form a right triangle. And because D and dx are known, the angle θx is related to D by tan θx=dx/D and θx can be calculated using the formula:

$$\theta x = \tan^{-1}(dx/D) \quad (1)$$

One of ordinary skill in the art would readily understand that the order in which the two line images are taken is not important. In other words, the line image for the reference collimator can be taken first or after the line image for the collimator 8 being measured. By repeating the steps described above along the y axis of the collimator 8, the angular orientation of the collimator hole in the y direction can be measured.

One of ordinary skill in the art would readily understand that the accuracy of the measured hole angle $\theta x$ is dependent upon the accuracy of the collimator holes in the parallel hole reference collimator. However, there is a class of parallel hole collimators, whose holes are all aimed substantially orthogonal to the collimator surface. These collimators tend to have much better dimensional accuracy and the holes are aimed true to their intended direction and the inventors have found that they do not substantially affect the accuracy of the measured hole angle $\theta x$. In one embodiment, the parallel hole reference collimator would have a dimensional tolerance of less than ±0.12 degrees.

In order to measure the orientation angle of all of the collimator holes along the x axis, one can capture images of the line radiation source 2 through all of the collimator holes along the x axis by scanning the line radiation source 2 in multiple steps across the width of the collimator 8/detector 6 assembly along the x axis and take images at each stepped position 2'. This scanning/stepping movement of the line radiation source 2 relative to the collimator 8/detector 6 assembly and the detector can be accomplished using an X-Y stage. Preferably an automated programmable X-Y stage would be used to enable the relative movement between the line radiation source 2 and the collimator 8/detector 6 assembly. In the example where a parallel hole reference collimator is used for determining the location of the reference position $X_1$, the scanning/stepping would need to be performed once with the parallel hole reference collimator and once with the collimator 8 being measured. However, because a collimator generally has hundreds of holes across its width, this process can take a long time using one line radiation source.

Thus, in a practical application of the method, a plurality of line radiation sources as shown in FIG. 2 can be used. FIG. 2 shows a carrier 14 holding a set of a plurality of line radiation sources 2 positioned in parallel relation and separated by a fixed distance W. According to a preferred embodiment, the line radiation sources 2 are provided in sufficient number to cover the width of the collimator 8. For purpose of discussion, we use an example where 20 line radiation sources that are spaced 2 cm apart on the carrier 14 sufficiently spans the width of the collimator 8. In this embodiment, the carrier 14 is scanned across the width of the collimator 8 in 2 mm stepped increments. At 2 mm increments, a total of ten discrete steps are all that is necessary to scan the whole width of the collimator 8.

At each stepped position, an image of the plurality of line radiation sources 2 is taken using the detector 6 similar to the single line radiation source example discussed above in connection with FIG. 1A. Thus, a set of images of the line radiation sources 2 are produced corresponding to each stepped position. These images will be referred to herein as "line images." At each discrete stepped position of the plurality of line sources 2 during this scanning/stepping, the mechanical position (in the x-y coordinate of the collimator 8) of the line sources 2 and the line images obtained by the detector 6 are stored in a suitable storage medium provided in the controller system that is carrying out the scanning. Similar to the single line radiation source example, the scanning/stepping procedure producing the set of line images is performed once with the collimator 8 being measured and, in the preferred embodiment and, again with a parallel hole reference collimator. The two scanning/stepping procedures, one with the reference collimator and the other with the collimator being measured, are carried out so that the mechanical positions for the plurality of line radiation sources 2 at each of the stepped interval are same in both scanning/stepping procedures. That is, the crucial requirement is that the spatial locations of the lines in both acquisition steps are repeatable. Alternatively, in the case of a single collimator acquisition, the reference positions $X_1$ of each line must be known a priori in terms of the position setting of the automated programmable X-Y stage scanning the lines over the detector.

Figure 3A:
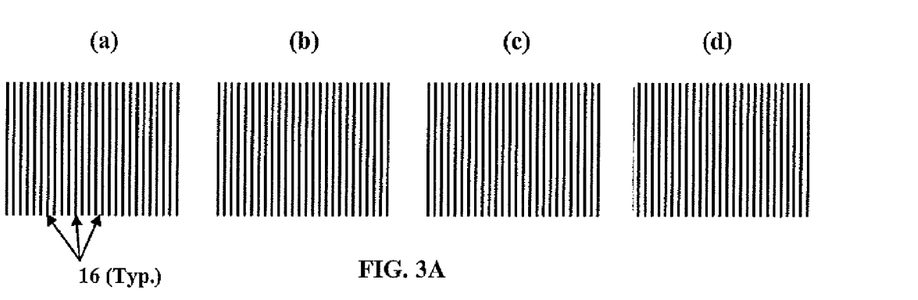
FIG. 3A shows a series of line images representing a series of the reference positions $X_1$ in the x-axis direction in the collimator's x-y coordinate plane.
Figure 3B:
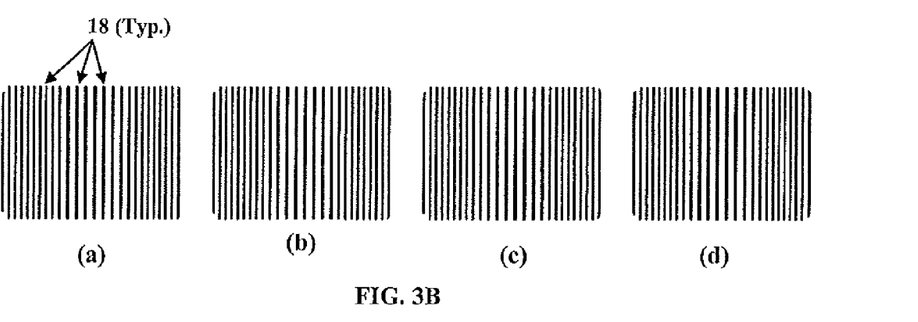
FIG. 3B shows a series of line images representing a series of the measured positions $X_2$ in the x-axis direction in the collimator's x-y coordinate plane.

The scanning/stepping performed with the parallel hole reference collimator generates a set of line images representing a series of the reference positions $X_1$. The scanning/stepping performed with the collimator 8 generates a set of line images representing a series of the measured positions $X_2$. FIG. 3A shows an example of the series of line images 16 representing a series of the reference positions $X_1$. FIG. 3B shows an example of the series of line images 18 representing a series of the measured positions $X_2$. In other words, FIG. 3A is a series of images of the intensities of collimated radiation impinging on the detector 6 for the parallel hole reference collimator, while FIG. 3B is the corresponding series of images of the intensities of collimated radiation impinging on the detector 6 for the variable focal length fan collimator 8 positioned at the same locations over the detector. The line images (a)-(d) in both sets of images represent the images taken at first four of the ten stepped intervals. In this embodiment, going from left-to-right, the entire carrier 14 holding the plurality of line radiation sources is translated by two millimeters per step, such that, after ten steps the collimator 8 has been sampled in two millimeter increments in the x axis direction.

The distance dx is obtained by noting the difference in the positions of respective lines in the two series of images. However, because each line in the line images are produced by multiple rows of detector pixels, each line is a raw image of ~10-15 pixels wide (along x axis) having approximately Gaussian, bi-Gaussian profile along the x axis direction for the parallel and variable fan collimators, respectively. Therefore, the position of the lines ($X_1$ and $X_2$) along the x axis direction at a given detector pixel position in the y axis direction must be determined by finding the "peak" of the imaged line's intensity profile in the x direction ("x-profile"). At each line's y axis position (along the y-dimension or vertical in the images of FIGS. 3A and 3B), the peak of the imaged line's x-profile can be determined by standard peak locating techniques. These include fitting a Gaussian/bi-Gaussian curve to the line's x-profile, or other peak location metrics.

In an alternate embodiment, the reference position $X_1$ can be determined without the use of a reference collimator. The reference position $X_1$ can be determined from the automated programmable X-Y stage being used for the scanning/stepping motion of the line radiation source 2 relative to the collimator 8/detector 6 assembly. For example, by calibrating the programmable X-Y stage's position relative to the collimator 8/detector 6 assembly or ensuring that the dimensional tolerances of the all components of the X-Y stage, collimator holder, and the detector, etc. the reference position $X_1$ can be determined from the position of the automated programmable X-Y stage itself. This alternate embodiment will be referred to hereinafter as the single collimator acquisition since the reference collimator is not needed.

After the dx values for each of the line images in FIGS. 3A and 3B are calculated, the collimator hole angles $\theta x$ along the x axis direction can be calculated using the equation (1) discussed above. It would be obvious to one or ordinary skill in the art that the collimator hole angles $\theta y$ along the y axis direction for the variable focal length fan beam collimator 8 can be calculated by repeating the scanning/stepping process described above in the y axis direction using the parallel hole reference collimator and the variable focal length fan beam collimator 8. That process would generate another set of series of line images similar to those shown in FIGS. 3A and 3B, from which dy values (analogous to dx values) can be calculated and then the orientation angles θy along they axis direction can be calculated using the formula:

$$\theta y = \tan^{-1}(dy/D).$$

The scanning/stepping process for they axis direction would be carried out by rotating the carrier 14 by 90 degrees so that the plurality of line radiation sources 2 are now oriented orthogonal to the orientation shown in FIG. 1B. This will allow the plurality of line radiation sources 2 to be scanned/stepped across the collimator 8 along its width in they axis direction. (See FIG. 1B for the x-y axis orientation).

Again, in the alternate single collimator acquisition embodiment, the reference positions $Y_1$ necessary for determining the offset distance dy in the y-direction can be determined without the use of a reference collimator.

The offset distance dx data from x-axis scan and dy from the y-axis scan are combined to generate a data set, vector map, of the collimator holes in the collimator 8. The vector map would include the θx and θy values for each hole of the collimator 8. The vector map is stored as part of the firmware associated with the particular collimator 8 so that a particular SPECT system in which the collimator 8 is installed, the SPECT system would be able to utilize the collimator's vector map data to accurately perform forward and/or back projection in reconstructing the SPECT image.

Figure 4:
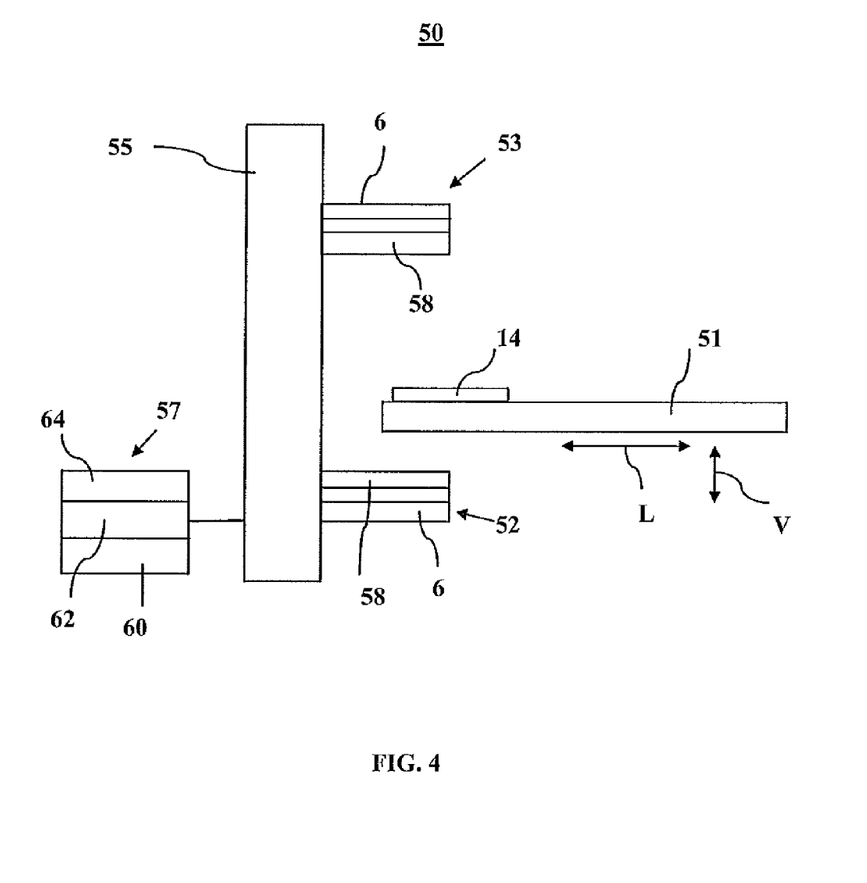
FIG. 4 is a schematic illustration of a dual-headed SPECT detector system that can be utilized to implement the arrangement 10 of FIG. 1A.

FIG. 4 is an example of a system 50 that can be utilized to implement the arrangement 10 of FIG. 1A. In this example, the system 50 is a SPECT system comprising at least a patient bed 51, detector units 52, 53, a gantry 55 providing support for the detector units 52, 53 and a control unit 57. The patient bed 51 is configured and adapted to be controllably movable in axial directions L, as well as vertical direction V. The patient bed 51 is used to hold the patient during the normal operation of the SPECT system, however, in this embodiment, the SPECT system 50 is utilized for the method described herein and the patient bed 51 is utilized as the movable stage on which the carrier 14 is mounted for performing the scanning/stepping procedure. The axial movement of the patient bed 51 in the direction L includes the directions along the y axes in the collimator's x-y coordinate plane. The scanning/stepping procedures in the x and y directions described above can be achieved by rotating the carrier 14 by 90° on the patient bed 51. The distance D is controlled by the patient bed's movement in the vertical direction V and detector head 53 radius. The detector unit 53 generally comprises a collimator 58 and a detector 6. The operation of the system 50 and the movement of the patient bed and the detector unit 53 are controlled by the control unit 57. The control unit 57 is provided with appropriate processor units 60, machine-readable memory units 62, and user interface units 64 for proper functioning of the system 50.

According to the alternate embodiment described above, a dedicated X-Y stage can be used to scan the line sources/carrier over a detector whose coordinates are calibrated relative to those of the X-Y stage, obviating the need for a reference scan with parallel collimator.

According to another embodiment, the arrangement 10 of FIG. 1A can be implemented on the SPECT system 50 by mounting the array 14 to the patient bed 51. The parallel hole collimator and the collimator 8 to be measured are positioned in place of the collimator 58 of detector unit 53. The motion of the movable patient bed 51 in a SPECT system 50 can be accurately controlled and thus can be used for the scanning/stepping process by moving the array 14 in stepped increments over the detector unit 52, for example, while maintaining the distance between the array 14 and the interaction plane 4 of the detector 6 to the fixed distance D. The data collected by the detector 6 would be processed and stored in the control unit 57 so that the processor units 60 can carry out the methods described above for calculating the dx, θx and dy, θy. The series of line images such as those shown in FIGS. 3A, 3B would be generated by the processor units 60 and stored in machine-readable memory units 62.

Accuracy of the system can be increased by an iterative process whereby the pixel location in the direction orthogonal to the focusing direction is re-computed using the map of the orthogonal direction angles. Details of such second order processes will vary with type of focusing collimation, but are obvious to those skilled in the art.

As noted, the embodiments described herein utilized a variable focal length fan beam collimator 8 as an example but, it will be appreciated that the disclosed system and method can be used to measure the hole angles of a variety of collimator types.

Figure 5:
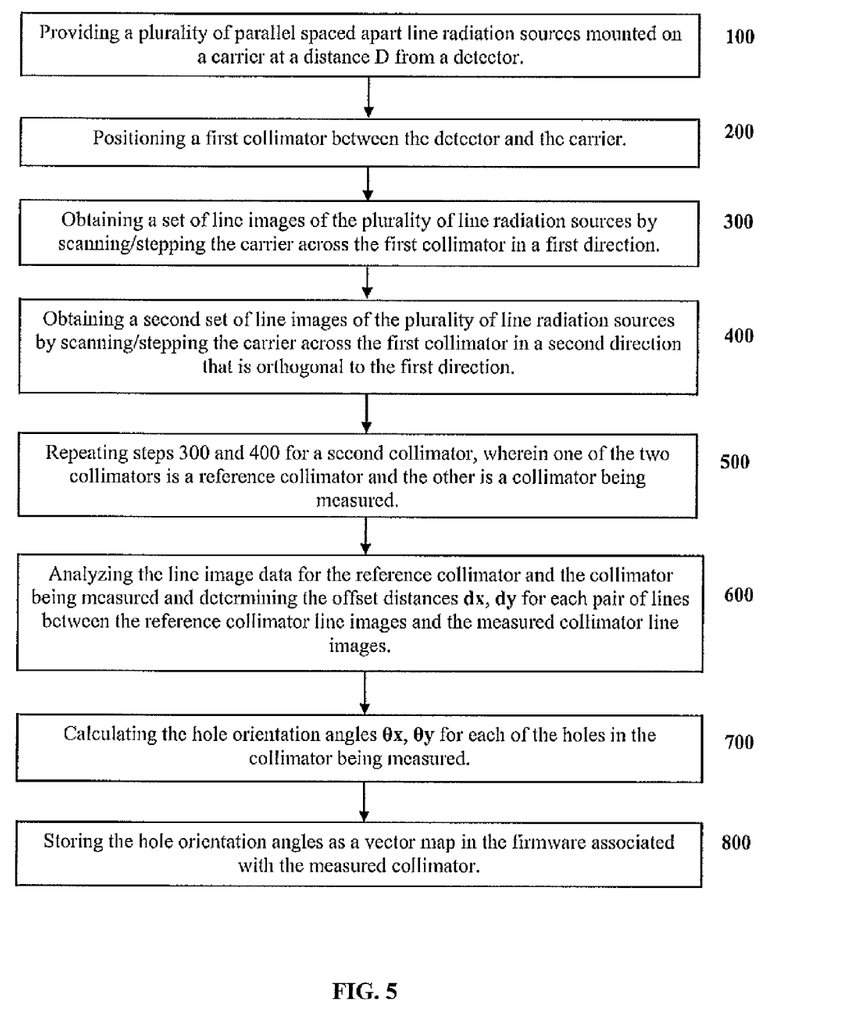
FIG. 5 is a flowchart describing a method of determining collimator hole angle using scanning nuclear line sources.

FIG. 5 is a flowchart summary of the method of the present disclosure according to an embodiment. The method of measuring the hole orientation angles of a collimator comprises providing a plurality of parallel spaced apart line sources 2 mounted on the carrier 14 at distance D from the interaction plane 4 of the detector 6. (See box 100). A first collimator is then positioned between the detector 6 and the carrier 14. (See box 200). A set of line images of the plurality of line radiation sources is obtained by scanning/stepping the carrier 14 across a first collimator in a first direction, wherein the first direction is one of the x or y direction in the collimator's x-y coordinate. (See box 300). As described above, the scanning/stepping procedure requires the carrier 14 to be stepped across the width of the collimator in stepped increments. Next, a second set of line images of the plurality of line radiation sources is obtained by scanning/stepping the carrier 14 across the first collimator in a second direction that is orthogonal to the first direction. (See box 400). Thus, if the first direction was along the x direction, the second direction would be along they direction and vice versa. In one embodiment, the scanning/stepping in the second direction is carried out by first rotating the carrier 14 90-degrees in the x-y plane. Next, the procedures of the boxes 300 and 400 are repeated for a second collimator, wherein one of the two collimators is a reference collimator (e.g. the parallel hole reference collimator discussed above) and the other of the two collimators is the measured collimator (the collimator being measured, e.g. the variable focal length fan beam collimator 8 discussed above). (See box 500). The line image data are analyzed for the reference collimator and the collimator being measured to determine the offset distances dx, dy for each pair of lines between the reference collimator's line image data and the measured collimator's line image data. (See box 600). Next, the hole orientation angles θx, θy for each of the holes in the measured collimator are calculated per formula (1) discussed above. (See box 700). The hole orientation angles θx, θy are stored as a vector map in the firmware associated with the measured collimator.

It will be appreciated that although the disclosed embodiments describe scanning/stepping the plurality of line radiation sources 2 with respect to the collimator and detector 6, it is contemplated that the line sources 2 can instead be held stationary and the collimator and detector 6 can be moved in stepped increments. The important point is that the line radiation sources 2 and the collimator and the detector 6 can be controllably stepped across with respect to each other to generate the series of line images from the collimated radiation impinging on the detector 6 and that the scan locations of first and second collimator are repeatable.

It will be appreciated that although the disclosed embodiments describe scanning/stepping the plurality of line radiation sources 2 with respect to the collimator to be measured and also with respect to a reference collimator, the scan with the reference collimator can be obviated by careful calibration of an accurate X-Y stage with respect to a detector over which the lines are scanned.

The method for operating the disclosed arrangement, as described herein, may be automated by, for example, tangibly embodying a program of instructions upon a machine-readable storage media, such as the machine-readable storage unit 62 of the SPECT system 50, capable of being read by a machine, such as the processor unit 60, capable of executing the instructions. A general purpose computer and/or computer processor is one example of such a machine. A non-limiting exemplary list of appropriate storage media well known in the art would include such devices as a readable or writeable CD, flash memory chips (e.g., thumb drives), various magnetic storage media, and the like.

The features of the system and method have been disclosed, and further variations will be apparent to persons skilled in the art. All such variations are considered to be within the scope of the appended claims. Reference should be made to the appended claims, rather than the foregoing specification, as indicating the true scope of the disclosed method.

The functions and process steps disclosed herein may be performed automatically or wholly or partially in response to user command. An activity (including a step) performed automatically is performed in response to executable instruction or device operation without user direct initiation of the activity.

The disclosed systems and processes are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of the disclosed system Further, any of the functions and steps provided in FIG. 5 may be implemented in hardware, software or a combination of both and may reside on one or more processing devices located at any location of a network linking the elements the disclosed system or another linked network, including the Internet.

Thus, although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for measuring a single photon emission computed tomography collimator's hole orientations, comprising:
    (a) providing a plurality of parallel spaced apart line radiation sources at a distance from a detector;
    (b) positioning a first collimator between the plurality of spaced apart line radiation sources and the detector;
    (c) obtaining a first set of line images of the plurality of line radiation sources by scanning/stepping the plurality of line radiation sources across the first collimator in a first direction;
    (d) obtaining a second set of line images of the plurality of line radiation sources by scanning/stepping the plurality of line radiation sources across the first collimator in a second direction that is orthogonal to the first direction;
    (e) repeating the steps (c) and (d) for a second collimator, wherein one of the two collimators is a reference collimator and the other of the two collimators is a collimator being measured, whereby the line images obtained using the reference collimator are reference collimator line images and the line images obtained using the collimator being measured are measured collimator line images;
    (f) analyzing the reference collimator line images and the measured collimator line images and determining the offset distance dx between the reference collimator line images and the measured collimator line images in the first direction and the offset distance dy between the reference collimator line images and the measured collimator line images in the second direction, wherein dx is the offset distance in the first direction and dy is the offset distance in the second direction; and
    (g) calculating hole orientation angles θx, θy for each collimator hole in the collimator being measured.

2. The method of claim 1, further comprising storing the hole orientation angles θx, θy as a vector map in a firmware associated with the collimator being measured.

3. The method of claim 1, wherein the reference collimator is a parallel hole collimator.

4. The method of claim 1, wherein the collimator being measured is a variable focal length fan beam collimator.

5. The method of claim 1, wherein the step (g) comprises calculating the angles θx, θy using the formula: $\theta(x,y)=\tan^{-1}(d(x,y)/D)$, wherein D is the distance between the plurality of line radiation sources and the detector.

6. A system for measuring a single photon emission computed tomography collimator's hole orientations comprising:
    a detector;
    a controllably movable stage;
    a plurality of parallel spaced line radiation sources positioned at a distance from the detector, wherein the plurality of line radiation sources are mounted on the controllably movable stage;
    a first collimator positioned between the detector and the plurality of line radiation sources;
    a control unit for controlling the movable stage, said control unit comprising: a machine-readable memory unit for storing a set of instructions for performing a method for measuring the single photon emission computed tomography collimator's hole orientations; and a processor unit for executing the set of instructions, wherein when said processor executes said set of instructions, the control unit performs said method comprising:
        (a) obtaining a first set of line images of the plurality of line radiation sources by scanning/stepping the plurality of line radiation sources across the first collimator in a first direction;
        (b) obtaining a second set of line images of the plurality of line radiation sources by scanning/stepping the plurality of line radiation sources across the first collimator in a second direction that is orthogonal to the first direction;
        (c) repeating the steps (a) and (b) for a second collimator, wherein one of the two collimators is a reference collimator and the other of the two collimators is a collimator being measured, whereby the line images obtained using the reference collimator are reference collimator line images and the line images obtained using the collimator being measured are measured collimator line images;

(d) said processor analyzing the reference collimator line images and the measured collimator line images and determining the offset distance dx between the reference collimator line images and the measured collimator line images in the first direction and the offset distance dy between the reference collimator line images and the measured collimator line images in the second direction; and (e) said processor calculating hole orientation angles $\theta x$, $\theta y$ for each collimator hole in the collimator being measured.

7. The system of claim 6, wherein said method further comprising storing the hole orientation angles $\theta x$, $\theta y$ as a vector map in a firmware associated with the collimator being measured.

8. The system of claim 6, wherein the reference collimator is a parallel hole collimator.

9. The system of claim 6, wherein the collimator being measured is a variable focal length fan beam collimator.

10. The system of claim 6, wherein the step (e) of said method comprises calculating the angles $\theta x$, $\theta y$ using the formula: $\theta(x,y) = \tan^{-1}(d(x,y)/D)$, wherein D is the distance between the plurality of line radiation sources and the detector.

11. A method for measuring a single photon emission computed tomography collimator's hole orientations, comprising:

(a) providing a plurality of parallel spaced apart line radiation sources at a distance from a detector;

(b) positioning a collimator to be measured between the plurality of spaced apart line radiation sources and the detector;

(c) obtaining a first set of line images of the plurality of line radiation sources by scanning/stepping the plurality of line radiation sources at a plurality of stepped positions across the collimator in a first direction;

(d) obtaining a second set of line images of the plurality of line radiation sources by scanning/stepping the plurality of line radiation sources at a plurality of stepped positions across the collimator in a second direction that is orthogonal to the first direction, whereby the line images obtained using the collimator being measured are measured collimator line images;

(e) determining a reference position for each of the measured collimator line image from the stepped positions of the plurality of line radiation sources measured with respect to the detector;

(f) analyzing the measured collimator line images and determining the offset distances dx between the reference position and the measured collimator line images for each measured collimator line images in the first direction and the offset distances dy between the reference position and the measured collimator line images for each measured collimator line images in the second direction; and (g) calculating hole orientation angles $\theta x$, $\theta y$ for each collimator hole in the collimator being measured.

12. The method of claim 11, further comprising storing the hole orientation angles $\theta x$, $\theta y$ as a vector map in a firmware associated with the collimator being measured.

13. The method of claim 11, wherein the collimator being measured is a variable focal length fan beam collimator.

14. The method of claim 11, wherein the step (g) comprises calculating the angles $\theta x$, $\theta y$ using the formula: $\theta(x,y) = \tan^{-1}(d(x,y)/D)$, wherein D is the distance between the plurality of line radiation sources and the detector.

* * * * *